| United States Patent [19] | [11] Patent Number: 4,937,385 |
| --- | --- |
| Buchholz et al. | [45] Date of Patent: Jun. 26, 1990 |

[54] PROCESS FOR THE MANUFACTURE OF DIALKYL DISULFIDES AND POLYSULFIDES

[75] Inventors: Bernard Buchholz, Whitpain; Edward J. Dzierza, Philadelphia; Robert B. Hager, Collegeville, all of Pa.

[73] Assignee: Pennwalt Corporation, Philadelphia, Pa.

[21] Appl. No.: 195,246

[22] Filed: May 18, 1988

[51] Int. Cl.$^5$ .................................. C07C 148/00
[52] U.S. Cl. ........................... 568/26; 568/21; 568/72; 568/73
[58] Field of Search ................ 568/21, 26, 72, 73

[56] References Cited

U.S. PATENT DOCUMENTS

| | | | |
| --- | --- | --- | --- |
| 3,022,351 | 2/1962 | Mihm et al. | 568/26 |
| 3,036,133 | 5/1962 | Goshorn et al. | 568/73 |
| 3,314,999 | 4/1967 | Bapseres et al. | 568/26 |
| 3,755,461 | 8/1973 | Kvasnikoff et al. | 568/26 |
| 4,102,931 | 7/1978 | Buchholz | 568/73 |
| 4,119,550 | 10/1978 | Davis et al. | 568/72 |
| 4,191,659 | 3/1980 | Davis | 568/21 |
| 4,313,006 | 1/1982 | Hager | 568/70 |
| 4,568,767 | 2/1986 | Dzierza et al. | 568/60 |
| 4,638,093 | 1/1987 | Fried | 568/73 |

*Primary Examiner*—Mary E. Ceperley

[57] ABSTRACT

A process is disclosed for continuously preparing dialkyl disulfides and dialkyl polysulfides by reacting at elevated temperature and in the presence of a solid, particulate catalyst an alkene and hydrogen sulfide in a first reaction zone, and then passing the reactor effluent into a second reaction zone where it is reacted at elevated temperature with molten, elemental sulfur in the presence of a solid, particulate catalyst.

23 Claims, 1 Drawing Sheet

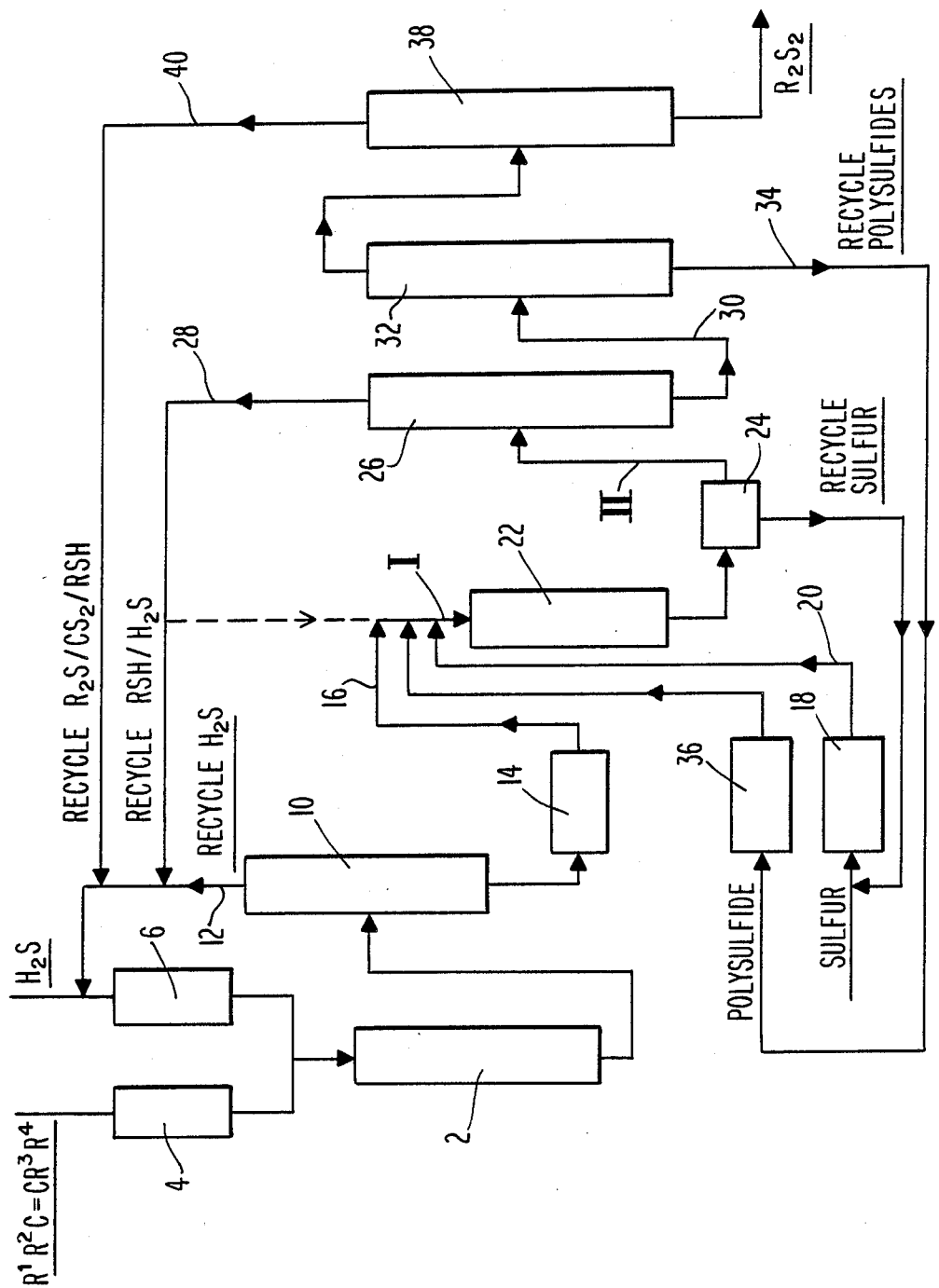

PROCESS FOR THE MANUFACTURE OF DIALKYL DISULFIDES AND POLYSULFIDES

BACKGROUND

This invention relates to a two reactor process for the continuous manufacture of dialkyl disulfides and polysulfides from alkenes, hydrogen sulfide ($H_2S$) and sulfur in the presence of solid particulate catalysts. More particularly, it relates to a process for the continuous manufacture of dialkyl disulfides and/or dialkyl polysulfides by reacting an alkene with $H_2S$ over a solid, particulate catalyst in a first reaction zone, and then passing the first reactor effluent into a second reaction zone, where it is reacted with elemental sulfur in the presence of a solid, particulate catalyst.

PRIOR ART

It is known that sulfur will oxidize mercaptans to the corresponding disulfides, according to equation (1), especially in the presence of an alkali, ammonia, or amine catalyst [E. E. Reid, Org. Chem. of Bivalent Sulfur, Vol. 1, p. 121 (1960)].

$$2RSH + S \rightarrow RSSR + H_2S \quad (1)$$

(where R=alkyl or aryl)

It is also known to react disulfides withh elemental sulfur to produce polysulfides, as shown in equation (2) [E. E. Reid, Org. Chem. of Bivalent Sulfur, Vol. 3, p. 389 (1960)].

$$RSSR + xS \rightarrow RSS_xSR \quad (2)$$

(where x=1, 2, 3, 4, ...)

The reactions of mercaptans with sulfur to produce disulfides [equation (1)] and of disulfides with sulfur to produce polysulfides [equation (2)] have been carried out exclusively in the liquid phase, usually with alkali or amine catalysts (U.S. Pat. No's. 3,314,999 and 3,755,461).

In the reaction of equation (1) it is necessary first to manufacture and isolate the mercaptan and then to oxidize it to the corresponding disulfide with sulfur. A direct preparation of dialkyl disulfides or polysulfides from alkenes, $H_2S$, and sulfur in a continuous manner has not been previously reported. Dialkyl polysulfide mixtures are prepared from alkenes, $H_2S$, and sulfur in a one-pot, batch process, wherein the preferred catalysts are ammonia or amines (U.S. Pat. No. 4,191,659). Relatively long reaction times (e.g., 10 to 12 hours) are required.

Continuous, vapor-phase processes to produce mercaptans from alkenes and hydrogen sulfide over solid, particulate catalysts, according to equation (3) are, of course, well known (U.S. Pat. No's. 4,102,931 and 3,036,133).

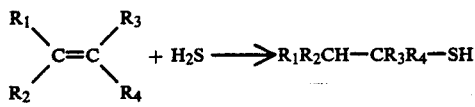

In related copending application Ser. No. 733,551, filed May 13, 1985, now abandoned it is disclosed that dialkyl disulfides can be produced continuously in a two-reactor process from alkanols, $H_2S$, and sulfur. The preferred catalyst is a sodium Type Y zeolite. The commercial manufacture of dialkyl disulfides by this process is, of course, limited to those compounds derived from readily available alkyl alcohols.

STATEMENT OF THE INVENTION

This invention is directed to a method of continuously manufacturing di-($C_2$–$C_{20}$) alkyl disulfides and di-($C_2$–$C_{20}$) alkyl polysulfides comprising continuously reacting a $C_2$–$C_{20}$ alkene and $H_2S$ over a solid, particulate catalyst in a first reaction zone at elevated temperature whereby an effluent product containing a $C_2$–$C_{20}$ alkyl mercaptan is continuously formed, and then continuously reacting over a solid, particulate catalyst in a second reaction zone the effluent product with molten, elemental sulfur at elevated temperature whereby the major product continuously formed is a di($C_2$–$C_{20}$) alkyl disulfide or polysulfide. The process can be directed solely to the production of dialkyl disulfides by recycling the dialkyl polysulfides that are formed to the second reactor, where they will react further with the mercaptan from the first reactor in a disproportionation reaction, to produce dialkyl disulfides. Conversely, the process can be directed to favor dialkyl polysulfides by employing higher sulfur:mercaptan molar ratios in the second reaction zone.

DETAILED DESCRIPTION OF THE INVENTION

A continuous process is provided for the economical manufacture of dialkyl disulfides or dialkyl polysulfides on a commercial scale.

The two-reaction zone process for the continuous preparation of dialkyl disulfides is described by equations (4) and (5), and the overall process is summarized by equation (6) below, where $R_1$, $R_2$ $R_3$, and $R_4$ are, independently, hydrogen, or $C_1$ to $C_{18}$ alkyl, cycloalkyl, or aralkyl groups.

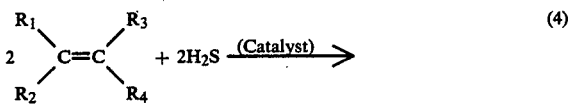

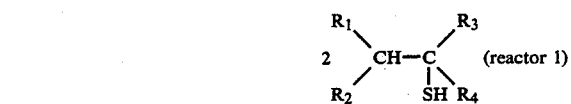

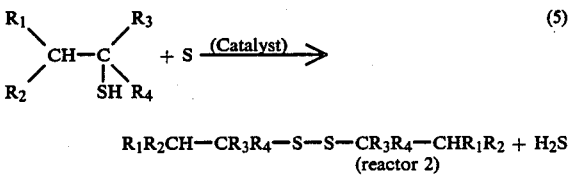

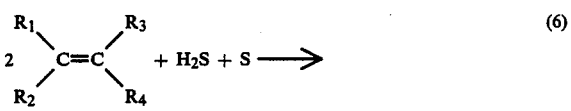

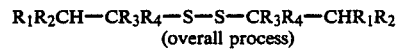
(overall process)

The alkenes which are useful for this invention have from 2 to 20 carbon atoms and will include, for example, ethene, propene, butene, pentene, hexene, heptene, octene, nonene, decene, undecene, dodecene, tetradecene, heptadecene octadecene and eicosene. In addition, the alkenes may be cyclic compounds, for example, cyclopentene, cyclohexene, cycloheptene, cyclooctene, and cyclododecene, or they may be aryl substituted compounds, for example styrene, methylstyrene, and ethylstyrene. The preferred alkenes for this invention have from 2 to 12, most preferably from 8 to 12 carbon atoms and may be straight or branch chained compounds.

The temperature range at which the reaction in the first reaction zone is carried out is generally from about 40° to about 450° C., preferably from about 80° to 350° C. The temperature range at which the reaction in the second reaction zone is carried out is generally between about 125° and about 400° C., preferably about 125° to 250° C. and most preferably between about 125° and 225° C. The reaction temperature in both zones is preferably controlled by the temperature of the heated catalyst bed through which the reactants pass although the reactants are usually preheated before being passed into the first reaction zone.

The pressure range at which the reaction in the first reaction zone is carried out is generally between about atmospheric and about 800 psig, and preferably between about 100 and about 400 psig. The pressure range at which the reaction in the second reaction zone is carried out is generally between about atmospheric and about 600 psig, and preferably between about 50 and 375 psig.

The molar ratio of alkene to H$_2$S in the first reaction zone ranges from about 1:2 to 1:20, the excess H$_2$S being used to depress the formation of by-product dialkyl sulfide. The preferred molar ratio range of alkene to H$_2$S will be from about 1:5 to about 1:10. The molar ratio of alkyl mercaptan to elemental sulfur, for reaction in the second reaction zone, ranges between about 1:0.05 to about 1:3, preferably between about 1:0.05 to 1:2 and most preferably between 1:0.1 and 1:2.

The molar velocity of the alkene passing through the catalyst in the first reaction zone may vary over a wide range but will usually be between about 25 and about 500, preferably between about 50 and 150 gram-moles of alkene per kilogram of catalyst per 24 hours (at standard temperature and pressure). The volume of the catalyst in the first zone is adjusted to produce mercaptan at the desired rate for passage of the effluent product to the second reaction zone. The molar velocity of the alkyl mercaptan, in the effluent product from the first reaction zone, passing over or through the catalyst in the second reaction zone will generally range from about 10 to about 2000, preferably from about 25 to 1250 gram-moles per kilogram of catalyst per 24 hours.

The reactions in both reaction zones of this invention, under the conditions of the prescribed process, with the exception of the molten elemental sulfur reactant, proceed in the vapor phase when the alkene reactant contains from 2 to 8 carbon atoms. The alkenes having in excess of 8 carbon atoms generally react in the form of a vapor-liquid mixture or mist.

The preparation of dialkyl polysulfides (trisulfides, tetrasulfides, pentasulfides, etc.) can be favored in this process by employing higher molar ratios of sulfur in the second reactor. In this case, the disulfide formed in the process reacts further with the excess elemental sulfur, by an insertion reaction, in the presence of the solid, particulate catalyst, to favor the formation of polysulfide mixtures, as shown in equation (7), where x=1 to 6.

$$R_1R_2CH-CR_3R_4-S-S-CR_3R_4-CHR_1R_2+xS \rightarrow R_1R_2CH-CR_3R_4-S-S_x-S-CR_3R_4-CHR_1R_2 \quad (7)$$

When R$_1$, R$_2$, R$_3$ and R$_4$ are all hydrogen, for example, the process can be utilized to prepare diethyl disulfide (DEDS) from ethylene, H$_2$S, and elemental sulfur, according to to equations (4), (5), and (6) above. When R$_1$, R$_2$, R$_3$ and R$_4$ are alkyl or hydrogen, with at least one being an alkyl group, as, for example, with the well-known alkene raw material "propylene trimer" (C$_9$H$_{18}$ or nonene), the process can be utilized to prepare di-tertiary-nonyl polysulfide (TNPS) mixtures from propylene trimer, H$_2$S, and sulfur, according to equations (4), (5), (6) and (7).

DEDS is a well-known article of commerce, being used as a chemical intermediate in the manufacture of agricultural compounds in lieu of ethyl mercaptan. Dialkyl disulfides are also useful as presulfiding agents for treatment of hydrodesulfurization catalysts in petroleum refining. TNPS is a well-known article of commerce, being used as an extreme-pressure (E.P.) lube additive, and particularly as an additive for cutting oils and lubricants.

Any of a number of conventional catalysts, such as alumina, silica, alumina-silicates, thoria, chromia, zeolites (U.S. Pat. No. 4,102,931), or alumina promoted with an alkali metal heteropoly acid salt, such as potassium phosphotungstate (U.S. Pat. No. 3,036,133), may be used in the first reaction zone to convert the C$_2$ to C$_{20}$ alkenes to C$_2$ to C$_{20}$ alkyl mercaptans. Zeolite catalysts are preferably used in the second reaction zone, where the crude, unisolated C$_2$ to C$_{20}$ alkyl mercaptan, in the vapor phase, is reacted with elemental sulfur, in the molten phase, to form a di-(C$_2$ to C$_{20}$) alkyl disulfide or polysulfide. Type X, Type Y, or Type L zeolites containing at least 3 percent of an alkali metal (e.g., Na) expressed as the oxide (e.g., Na$_2$O), are preferred catalysts.

The zeolite catalysts preferred in the second reaction-zone are synthetic aluminosilicates characterized by high uniformity, well-defined pore size, large surface area, and complete crystallinity and are further defined, for example, in U.S. Pat. No. 4,281,202.

The zeolites, as prepared, generally contain as the cation about 13 percent by weight sodium (as Na$_2$O) or equivalent amount of other alkali metal. This cation may be replaced with other cations to reduce the sodium content. In this invention, however, the preferred catalyst contains sodium as the cation, with a sodium content of at least 3 percent, preferably more than 5 percent, more preferably greater than 10 percent, and most preferably at the 13 percent by weight (as Na$_2$O) level.

The most preferred catalysts for the second reaction zone are the Type Y synthetic zeolites which contain about 13 percent sodium (expressed as Na$_2$O) by weight as the cation. An example of a commercially available catalyst of this type is the Linde LZ-Y52 molecular sieve catalyst manufactured by Union Carbide Corporation.

THE DRAWING

The process of this invention is shown generally in the drawing which is a flow diagram for the manufacture of dialkyl disulfides and/or polysulfides. An alkene and H$_2$S are fed continuously in a molar ratio ranging from 1:2 to 1:20, to the reactor 2, the excess H$_2$S being used to depress the formation of by-product dialkyl sulfide. The reactants are heated and vaporized in preheaters 4 and 6, mixed, and fed to the first reactor 2. A major portion of the H₂S can be separated readily from the effluent in the high-pressure separator 10 and returned to the first reactor via line 12. The remaining crude mercaptan in the effluent stream and sulfur are fed to the second reactor 22 through lines 16 and 20, respectively, in a molar ratio preferably ranging from about 1:0.05 to 1:0.15 at which level the amount of sulfur used is less than the stoichiometric requirement for the equation:

$$2RSH + S \rightarrow RSSR + H_2S$$

and which is used to minimize polysulfide formation and favor disulfide formation. With crude mercaptan to sulfur molar ratios of about 1:0.15 to 1:3, polysulfide formation is enhanced greatly.

The reactants, crude mercaptan and sulfur, are heated in preheaters 18 and 36, mixed, and passed into the second reactor 22 containing a zeolite catalyst. Elevated temperatures, in the range of 125° C. to 400° C., and pressures from atmospheric to 600 psig, are used to effect reaction. At these conditions, the crude mercaptan can be in the vapor or the liquid state and the elemental sulfur is in the molten state.

Any unreacted sulfur is separated at 24 from the crude product which is passed into a series of distillation columns (or towers). The first column 26 removes the low-boilers (unreacted alkene mercaptan and H₂S) in the overhead stream 28 and recycles them back to the reactor 2 or 22. The bottoms stream 30 is then passed to the second distillation tower 32 where the heavies, mostly polysulfides, are taken as a bottoms product (for polysulfide production) or recycled via line 34 through a pre-heater 36 back to the second reactor 22 to react with the mercaptan to form more disulfide (e.g., $RSSSR + 2RSH \rightarrow 2RSSR + H_2S$). The remaining low-boilers and the product, a dialkyl disulfide, are taken as an overhead and passed to the third tower 38. The high-purity product, e.g., dialkyl disulfide, is taken off from tower 38 as a bottom material, while any remaining low-boilers are taken overhead through line 40 for recycle back to the first reactor, 2.

The molar ratio of fresh sulfur and fresh alkyl mercaptan (from reactor 2) fed to the system may range from a 3 to 1 molar excess of sulfur over alkyl mercaptan to a 10 to 1 molar excess of alkyl mercaptan over sulfur. The molar ratios in the combined fresh-plus-recycle feed to the reactor 22 may, of course, be outside this range, and for disulfide production, will usually contain a molar excess of alkyl mercaptan over sulfur, and may be as high as 20 to 1.

The feed to the reactor 22 may also contain 5 to 50 percent by volume of an inert gas or mixture of inert gases to provide sufficient heat removal from the catalyst zone. The inert gases may be nitrogen, methane, ethane, propane, butane, carbon dioxide, or any other gas that does not interfere with the reactions to produce the desired dialkyl disulfide or polysulfide.

The rate at which the alkyl mercaptan (from reactor 2) is passed over or through the solid, particulate catalyst may range from about 10 to about 2000, preferably 25-1250, gram-moles of alkyl mercaptan per kilogram of catalyst per 24 hours (or 10 to 2000, preferably 25-1250, pound-moles of alkyl mercaptan per 1000-lbs. of catalyst per 24 hours).

The preferred catalyst-bed temperatures (reaction temperatures) are in the range of 125°-250° C. and the preferred pressures in the reactor are in the range of 50-375 psig. The preferred molar ratio of alkyl mercaptan to sulfur fed into the reactor is in the range of 20:1 to 1:2, and is most preferably near the ratio of 7:1 for the manufacture of disulfides and near the ratio of 1:1-1.5 for the manufacture of polysulfides. The preferred dialkyl disulfides and dialkyl polysulfides for which this process is to be used, are the di($C_2$-$C_{12}$)-alkyl disulfides and polysulfides.

EXAMPLES

The following examples are intended to illustrate the novel process of this invention. In Example 1, the use of a preferred catalyst is demonstrated. In Example 2, the alkene ($C_2H_4$) is added to the feed to the second reactor 22 of the flow diagram to demonstrate that there is no detrimental effect when this impurity in the crude reactor effluent from the first reaction zone enters the second reaction zone. In Example 3, a synthetic mixture corresponding to the composition at point I in the flow diagram of the drawing is passed continuously over the catalyst, and the composition of the crude product (point II in the flow diagram) is determined by gas chromatographic (GC) analyses. The material balances across the reactor, and the single-pass conversions to dialkyl disulfide are calculated from the GC data for each example. In Example 4, the manufacture of di-t-nonyl disulfide and di-t-nonyl polysulfide is demonstrated.

EXAMPLE 1

The catalyst installed in reactor 22 of the flow diagram was Union Carbide's LZ-Y52, a sodium Type Y synthetic zeolite, ⅛" extrudate, bonded with 20% acid-washed inorganic oxide. To simulate the feed mixture of sulfur and effluent product from reactor 2 entering reactor 22 at Point I in the flow diagram, ethyl mercaptan, H₂S, and sulfur were pumped separately as liquids at appropriate rates to provide a mixture of $C_2H_5SH/H_2S/S$ in a molar ratio of approximately 1/0.5/0.15 continuously entering the reactor 22. The ethyl mercaptan and H₂S were vaporized in a preheater 14 prior to entering reactor 22.

The reactor 22 was a 316 stainless steel (SS) tube, 2-inches in diameter and 36-inches in length, enclosed in an electrically-heated, vertical furnace. The catalyst was in a fixed-bed arrangement, maintained in the temperature range 135°-160° C. The exit stream from reactor 22 was passed as a vapor into a SS vessel, represented by 24 in the flow diagram, maintained at 165° C. to separate unreacted sulfur from the crude product stream. The effluent was then cooled by passing the crude product through a coil immersed in a 60/40::ethanol/water bath maintained at −5° C., sufficient to completely liquify the crude. The liquified stream was then passed directly into liquid-sampling valves and injected directly into a gas chromatograph for analysis. The stream was visually inspected through a glass flow meter tube to confirm complete liquification, passed through a back-pressure controlled-release valve, and then into a collection vessel, maintained at 35° C., with a vent to a gas flare. The pressure in the reactor system was maintained between 325 and 340 psig, and the ethyl mercaptan mole velocity was maintained at about 1.0 kilogram-mole of $C_2H_5SH$ per kilogram of catalyst per 24 hours.

A series of 8 continuous runs of approximately 2-hours duration each are reported. The reaction conditions and production rates of the major products (in kilograms per kilogram of catalyst per 24-hours) are given for each run in Table 1. A series of gas chromatographic analyses were made of the effluent at Point II of the flow diagram during each run to obtain the production figures for each run.

The conversion of ethyl mercaptan to DEDS was calculated as the moles of $C_2H_5SH$ used to produce DEDS, divided by the moles of $C_2H_5SH$ fed. As shown in Table 1, 19.8 to 35.2 percent of the ethyl mercaptan fed was converted to DEDS in a single pass. The production rate of DEDS ranged from 11.0 kilograms to almost 22.0 kilograms of DEDS per kilogram of catalyst per 24 hour day, with a temperature range of 135°–145° C., and an ethyl mercaptan mole velocity of approximately 1.0 kilogram-mole per kilogram of catalyst, per 24-hour day. Production rates of $C_2H_5S_3C_2H_5$ (DES3) and $C_2H_5S_4C_2H_5$ (DES4) are in the range 1.0–3.5 kilograms of DES3 per kilogram of catalyst per 24 hour day and 0.10–0.64 kilogram of DES4 per kilogram of catalyst per 24 hour day. Neither $CS_2$ (carbon disulfide) nor $C_2H_5SC_2H_5$ (diethyl sulfide) were detected in the process stream.

low levels, the conversion of ethylene to DES was in the range of 31% in Run 6 to 56% in Run 2. No $CS_2$ was detected in the process effluent of any run. No change in production rate was observed when the run was repeated without ethylene (Table 3, Runs 1 and 2).

TABLE 2

| RUN | $C_2H_5SH$ IN | $H_2S$ IN | Sulfur IN | $C_2H_4$ IN | $H_2S$ OUT | $C_2H_4$ OUT | $C_2H_5SH$ OUT | DES OUT | DEDS OUT | DES3 OUT | DES4 OUT | % Conv. to DEDS |
|---|---|---|---|---|---|---|---|---|---|---|---|---|
| 1 | 60.14 | 19.73 | 5.13 | 0 | 14.96 | 0 | 34.29 | 0 | 23.01 | 2.85 | 0.27 | 38.9 |
| 2 | 63.31 | 15.23 | 5.25 | 1.51 | 11.92 | 0.66 | 37.15 | 2.00 | 23.23 | 2.11 | 0.18 | 37.3 |
| 3 | 63.50 | 21.70 | 4.97 | 0 | 16.17 | 0 | 40.36 | 0 | 20.68 | 3.09 | 0.39 | 33.1 |
| 4 | 71.33 | 45.80 | 4.71 | 1.51 | 30.16 | 0.71 | 42.02 | 1.44 | 25.64 | 5.07 | 0.79 | 36.5 |
| 5 | 62.44 | 18.16 | 4.84 | 0 | 14.57 | 0 | 40.01 | 0 | 20.29 | 2.58 | 0.23 | 33.0 |
| 6 | 53.80 | 12.26 | 4.77 | 1.51 | 13.80 | 1.04 | 39.99 | 1.07 | 12.50 | 0.49 | 0.05 | 23.6 |

Values are in kilograms/kilogram of catalyst/24-hours.
DEDS is diethyl disulfide
DES3 is diethyl trisulfide
DES4 is diethyl tetrasulfide
DES is diethyl sulfide

EXAMPLE 3

The conditions of Example 1 were repeated, except that a simulated diethyl polysulfide recycle was fed to the second reactor 22 along with the simulated fresh feed from the first reactor 2. This resulted in a mixture of $C_2H_5SH/H_2S/S/DES_x$ in the approximate molar ratio of 1/0.5/0.15/0.02 to 1/0.5/0.15/0.04 being fed to reactor 22 at point I in the flow diagram. The remaining operating conditions were comparable to those in Example 1. The results of the runs of Example 3 are reported in Table 3. In runs 4 and 7, the production rates of DEDS were the highest observed (29.9 and 33.2 kilograms of DEDS per kilogram-catalyst per 24-hours, respectively). The outputs of diethyl polysulfides in the reactor effluent were observed to be lower than the inputs in all runs, demonstrating that equilibrium is achieved at relatively low polysulfide recycle rates (e.g., 2.4 to 4.5 kilograms of recycle DES3 per kilogram of catalyst per 24-hour day and 0.70 to 1.40 kilograms of

TABLE 1

| RUN | $C_2H_5SH$ IN | $H_2S$ IN | Sulfur IN | $H_2S$ OUT | $C_2H_5SH$ OUT | DEDS OUT | DES3 OUT | DES4 OUT | % Conv. to DEDS |
|---|---|---|---|---|---|---|---|---|---|
| 1 | 56.35 | 20.24 | 9.87 | 14.62 | 37.99 | 14.68 | 1.57 | 0.137 | 26.5 |
| 2 | 56.72 | 15.94 | 4.45 | 14.28 | 42.51 | 11.02 | 1.09 | 0.111 | 19.8 |
| 3 | 56.29 | 19.93 | 4.55 | 15.19 | 37.12 | 16.45 | 3.09 | 0.378 | 29.7 |
| 4 | 50.20 | 19.25 | 5.09 | 14.66 | 32.31 | 15.28 | 3.54 | 0.638 | 31.0 |
| 5 | 55.36 | 19.39 | 4.77 | 13.86 | 35.74 | 17.19 | 3.10 | 0.383 | 31.6 |
| 6 | 57.53 | 16.25 | 4.45 | 12.07 | 34.37 | 19.94 | 3.42 | 0.384 | 35.2 |
| 7 | 59.08 | 14.21 | 4.93 | 18.37 | 38.43 | 18.47 | 2.51 | 0.270 | 31.8 |
| 8 | 64.68 | 19.35 | 5.19 | 14.19 | 39.41 | 21.66 | 2.96 | 0.279 | 34.1 |

Values are in kilograms/kilogram catalyst/24-hours
DEDS is diethyl disulfide
DES3 is diethyl trisulfide
DES4 is diethyl tetrasulfide

EXAMPLE 2

Example 2 is similar to Example 1, except that ethylene was included in the feed to second reactor 22. The results of the runs of Example 2 are reported in Table 2. Ethylene is a possible stream component at Point I in flow diagram. With operating conditions comparable to those in Example 1 (except for higher $H_2S$-levels used in Runs 3 and 4), similar DEDS production rates were obtained (12.5 to 25.0 kilograms per kilogram of catalyst per 24 hour day). The single-pass conversion of ethyl mercaptan to DEDS remained high at 23 to 39%. When ethylene was fed to the second reactor 22, at relatively recycle DES4 per kilogram of catalyst per 24-hour day). Neither $C_2H_5SC_2H_5$ (DES) nor $CS_2$ were detected in the process effluent of any runs where the polysulfides were recycled. Conversion figures are not given in Table 3, since a substantial portion of the DEDS obtained is derived from the polysulfides that were recycled.

This example demonstrates the feasibility of operating the process of the flow diagram, with total recycling of the polysulfides DES3 and DES4, to produce diethyl disulfide as the major product of the process, and with essentially no net production of polysulfides.

TABLE 3

| RUN | $C_2H_5SH$ IN | $H_2S$ IN | Sulfur IN | DES3 IN | DES4 IN | $H_2S$ OUT | $C_2H_5SH$ OUT | DEDS OUT | DES3 OUT | DES4 OUT |
|---|---|---|---|---|---|---|---|---|---|---|
| 1 | 46.97 | 14.41 | 5.64 | 0 | 0 | 11.54 | 25.42 | 19.78 | 2.32 | 0.19 |
| 2 | 62.01 | 21.50 | 5.22 | 0 | 0 | 18.12 | 36.64 | 23.10 | 2.54 | 0.23 |
| 3 | 56.85 | 16.12 | 4.45 | 0.98 | 0.29 | 12.21 | 34.51 | 21.33 | 1.50 | 0.09 |
| 4 | 57.59 | 14.75 | 4.81 | 2.46 | 0.74 | 7.09 | 27.85 | 29.89 | 3.33 | 0.23 |
| 5 | 57.59 | 16.25 | 4.68 | 2.34 | 0.70 | 17.03 | 39.62 | 18.70 | 1.32 | 0.12 |
| 6 | 57.97 | 13.63 | 4.71 | 4.69 | 1.41 | 12.54 | 32.69 | 27.72 | 3.02 | 0.21 |
| 7 | 59.95 | 16.35 | 4.90 | 4.56 | 1.37 | 7.93 | 27.72 | 33.16 | 4.54 | 0.35 |

Values are in kilograms/kilogram of catalyst/24-hour day
DEDS is diethyl disulfide
DES3 is diethyl trisulfide
DES4 is diethyl tetrasulfide

EXAMPLE 4

Mixtures of tertiary-nonyl mercaptan (tert-$C_9H_{19}SH$), $H_2S$, and sulfur in various molar ratios were passed over a catalyst bed composed of Union Carbide's LZ-Y52 sodium Type Y zeolite and maintained at 123°–129° C. in a reactor as represented by numeral 22 in the flow diagram of the drawing. The pressure in the system was maintained at 325 psig. In this manner, the feed mixtures, which are theorized to exist at point I, were simulated in the process shown in the flow diagram when the process is utilized to produce di-tert-nonyl disulfide or polysulfide from propylene trimer (a branched nonene), $H_2S$, and sulfur. The reaction of propylene trimer with $H_2S$ in reactor 2 of the flow diagram, at well known process conditions, leads to tert-nonyl mercaptan.

The reactor 22 effluent was collected and $H_2S$ was separated. The remaining liquid product was analyzed by high-pressure liquid chromatography (HPLC). Analysis of the crude products obtained at the lower molar ratios of sulfur to tert-nonyl mercaptan (Table 4, Runs 1 and 2) showed them to be largely di-tert-nonyl disulfide and di-tert-nonyl trisulfide. HPLC analysis of product obtained at higher molar ratios of sulfur to tert-nonyl mercaptan (Table 4, Runs 3 and 4) were found to be mixtures of (tert-$C_9H_{19})_2S_x$, with x being 2–7 and 8. The results are shown in Table 4. In Runs 7–9, the beneficial effect of a higher sulfur to mercaptan ratio (0.8 to 1.0) on the conversion to di-tert-nonyl polysulfide (TNPS) was observed. However, the high level of sulfur feed resulted in operating problems due to sulfur plugging. Conversions in the table below were calculated from the weights of product collected in each run and their HPLC analysis.

TABLE 4

| Run No. | $C_9H_{19}SH$ IN | Sulfur IN | $H_2S$ IN | % Conversion, (Single-pass) 2 $C_9H_{19} \rightarrow (C_9H_{19})_2S_x$ |
|---|---|---|---|---|
| 1 | 634 | 188 | 282 | 30% |
| 2 | 529 | 99 | 282 | 20% |
| 3 | 407 | 227 | 704 | 33% |
| 4 | 374 | 145 | 798 | 27% |
| 5 | 582 | 133 | 188 | 22% |
| 6 | 812 | 116 | 289 | 28% |
| 7 | 499 | 502 | 266 | 53% |
| 8 | 499 | 414 | 329 | 45% |
| 9 | 497 | 490 | 223 | 64% |

Values in the above table are in gram-moles/kilogram of catalyst/24-hours.

Example 4 also includes a series of six runs (reported in Table 5) conducted at relatively high sulfur to mercaptan molar ratios (1.1–1.9), but much lower feed rates, to avoid sulfur plugging. Conversions to TNPS remained high (58–73%).

TABLE 5

| Run No. | $C_9H_{19}SH$ IN | Sulfur IN | $H_2S$ IN | % Conversion (Single-pass) 2 $C_9H_{18} \rightarrow (C_9H_{19})_2S_x$ |
|---|---|---|---|---|
| 1 | 65 | 73 | 63 | 66% |
| 2 | 52 | 88 | 35 | 71% |
| 3 | 26 | 40 | 35 | 73% |
| 4 | 97 | 157 | 23 | 71% |
| 5 | 24 | 46 | 19 | 58% |
| 6 | 76 | 101 | 49 | 60% |

Values in the above table are in gram-moles/kilogram of catalyst/24 hours

EXAMPLE 5

This example is similar to Example 4, except that propylene trimer, a nonene, was included in the feed to the second reactor 22. The results of the runs of Example 5 are reported in Table 6. Propylene trimer is a possible component of the feed stream at point I in the flow diagram. With operating conditions comparable to those in Example 4, (except that $H_2S$ levels were varied a gradual dropoff in TNPS conversion was obtained (63 to 41%; Table 6, runs 1 to 6) as the amount of nonene was increased (3 to 15%). When the nonene was fed to the second reactor 22, at relatively low levels, di-t-nonyl sulfide (DTNS) was formed. The conversion of nonene to DTNS was in the range of 11.6% (in Run 5) to 19.3% (in Run 1). No $CS_2$ was detected in the process effluent of any run.

TABLE 6

| Run No. | $C_9H_{18}$ IN | $C_9H_9SH$ IN | Sulfur IN | $H_2S$ IN | % Conversion (Single-pass) 2 $C_9H_{18} \rightarrow (C_9H_{19})_2S_x$ |
|---|---|---|---|---|---|
| 1 | 3 | 72 | 101 | 64 | 63% |
| 2 | 8 | 74 | 105 | 29 | 60% |
| 3 | 8 | 79 | 100 | 88 | 54% |
| 4 | 8 | 76 | 95 | 117 | 54% |
| 5 | 15 | 78 | 100 | 70 | 41% |
| 6 | 14 | 74 | 100 | 70 | 43% |
| 7 | 0 | 76 | 101 | 61 | 55% |

Values in the above table are in gram-moles/kilogram of catalyst/24 hours.

One advantage of this process over prior art processes is that it produces dialkyl disulfides or polysulfides from alkenes, rather than alkyl mercaptans, as a raw material, resulting in substantial cost savings on a commercial scale. Another advantage is that it provides a continuous process for dialkyl disulfide or polysulfide production. Still another advantage over earlier processes is the absence of the formation of by-product water. Another advantage over prior art processes is that the dialkyl disulfides or polysulfides can be manufactured with very little formation of by-product dialkyl sulfides or carbon disulfide. Another advantage is that the dialkyl polysulfides produced as co-products, are totally recyclable, allowing the process to be utilized for the production of dialkyl disulfides, exclusively. Another advantage is that high dialkyl disulfide or polysulfide production rates can be sustained for long periods of time without the necessity for air-regeneration of the catalyst to remove coke and tars.

We claim:

1. A process for the preparation of di($C_2$–$C_{20}$)alkyl disulfides and polysulfides which comprises continuously reacting over a solid, particulate catalyst in a first reaction zone a $C_2$–$C_{20}$ alkene with hydrogen sulfide at elevated temperature whereby an effluent product containing a $C_2$–$C_{20}$ alkylmercaptan is continuously formed, and then continuously reacting over a solid, particulate catalyst, which is a Type X, Type Y or Type L zeolite catalyst, in a second reaction zone said effluent product and molten, elemental sulfur at elevated temperature whereby the major product continuously formed is a di($C_2$–$C_{20}$)alkyl disulfide or polysulfide.

2. The process of claim 1 wherein the alkene is $C_2$ to $C_{12}$ alkene.

3. The process of claim 1 wherein a major proportion of any hydrogen sulfide in said effluent product is removed prior to reacting said effluent product in said second reaction zone.

4. The process of claim 1 wherein the zeolite catalyst is a Type Y zeolite.

5. The process of claim 4 wherein the Type Y zeolite catalyst is an alkali metal zeolite, containing from 3 to 13% by weight alkali metal, expressed as the alkali metal oxide.

6. The process of claim 5 wherein the alkali metal is sodium or potassium.

7. The process of claim 2 wherein the temperature in said second reaction zone is in the range of from 125° C. to 400° C. and the reaction is carried out under a pressure within the range of from about atmospheric to about 800 psig.

8. The process of claim 7 wherein the temperature in said second reaction zone is in the range of from 125° C. to 225° C. and the pressure is in the range of from 100 to 400 psig.

9. The process of claim 2 wherein the molar ratio of alkyl mercaptan to sulfur in said second reaction zone ranges from 1:0.05 to 1:3.

10. The process of claim 9 wherein the molar velocity of said alkyl mercaptan reacting in said second reaction zone ranges from 25 to 1250 gram-moles per kilogram of catalyst per 24-hours.

11. The process of claim 10 wherein the molar ratio of alkyl mercaptan to sulfur ranges from 1:0.15 to 1:3 and a dialkyl polysulfide is formed as the major product.

12. The process of claim 10 wherein the molar ratio of alkyl mercaptan to sulfur ranges from 1:0.05 to 1:0.15 and a dialkyl disulfide is formed as the major product.

13. The process of claim 2 wherein any unreacted sulfur present in the product from said second reaction zone is separated and recycled to said second reaction zone.

14. The process of claim 2 wherein any dialkyl polysulfide present in the product from said second reaction zone is separated and recycled to said second reaction zone, and dialkyl disulfide is collected as the principal product.

15. The process of claim 2 wherein any by-product dialkyl sulfide and carbon disulfide present in the product from said second reaction zone are separated and recycled to said first reaction zone.

16. The process of claim 2 wherein an inert gas is present in the reaction mixture at levels up to 50% by weight, in at least one of said reaction zones.

17. The process of claim 6 wherein the alkene is $C_2$ to $C_9$ alkene, the temperature in said second reaction zone is in the range from 125° C. to 225° C., the pressure in said second reaction zone is in the range from 100 to 400 psig, the molar velocity of the $C_2$ to $C_9$ alkyl mercaptan contained in said effluent product is in the range from 25 to 1250 gram-moles per kilogram of catalyst per 24-hours, and the molar ratio of elemental $C_2$ to $C_9$ alkyl mercaptan to elemental sulfur is in the range of from 1:0.1 to 1:2.

18. The process of claim 17 wherein at least a portion of any hydrogen sulfide present in said effluent product is removed therefrom whereby said effluent product contains no more than about 50% hydrogen sulfide based on the weight of said effluent product.

19. The process of claim 18 wherein the alkene is ethylene or nonene.

20. The process of claim 19 wherein diethyl or dinonyl polysulfide is separated from the product of said second reaction zone and continuously recycled to said second reaction zone.

21. The process of claim 19 wherein diethyl or dinonyl polysulfide is continuously collected as the principal product.

22. The process of claim 20 wherein the elevated temperature of said first reaction zone is between about 80° and 350° C. and the reaction in said first reaction zone is carried out at a pressure ranging from about 100 and 400 psig.

23. The process of claim 21 wherein the elevated temperature of said first reaction zone is between about 80° and 350° C. and the reaction in said first reaction zone is carried out at a pressure ranging from about 100 and 400 psig.

* * * * *